US008689648B1

(12) United States Patent
Heff

(10) Patent No.: US 8,689,648 B1
(45) Date of Patent: Apr. 8, 2014

(54) COMPACT AEROSOL SAMPLER

(75) Inventor: Allan Heff, Newton, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 555 days.

(21) Appl. No.: 12/322,961

(22) Filed: Feb. 6, 2009

(51) Int. Cl.
*G01N 1/24* (2006.01)

(52) U.S. Cl.
USPC .......... 73/863.22

(58) Field of Classification Search
None
See application file for complete search history.

(56) References Cited

U.S. PATENT DOCUMENTS

| | | | | |
|---|---|---|---|---|
| 3,966,439 | A * | 6/1976 | Vennos | 73/863.22 |
| 4,133,202 | A * | 1/1979 | Marple | 73/28.06 |
| 4,926,679 | A * | 5/1990 | Dewhurst | 73/28.05 |
| 4,972,957 | A * | 11/1990 | Liu et al. | 209/143 |
| 5,693,895 | A * | 12/1997 | Baxter | 73/863.22 |
| 6,101,886 | A * | 8/2000 | Brenizer et al. | 73/863.23 |
| 6,240,768 | B1 * | 6/2001 | Lemonnier | 73/28.05 |
| 6,431,014 | B1 * | 8/2002 | Liu et al. | 73/863.22 |
| 6,729,196 | B2 * | 5/2004 | Moler et al. | 73/863.22 |
| 7,458,284 | B2 * | 12/2008 | Shih et al. | 73/863.23 |
| 7,574,928 | B1 * | 8/2009 | Cole et al. | 73/863.22 |
| 7,597,015 | B2 * | 10/2009 | Harley | 73/865.5 |
| 2006/0127966 | A1 * | 6/2006 | Ryan | 435/30 |
| 2007/0044577 | A1 * | 3/2007 | Trakumas et al. | 73/863.22 |
| 2010/0089183 | A1 * | 4/2010 | Solomon | 73/863.22 |
| 2010/0288057 | A1 * | 11/2010 | Witham | 73/863.22 |

* cited by examiner

*Primary Examiner* — Robert R Raevis
(74) *Attorney, Agent, or Firm* — AFMCLO/JAZ; Fredric Sinder

(57) ABSTRACT

Provided is an aerosol collector of reduced size having an aerosol inlet, an impactor plate containing several particle size-selecting nozzles therethrough, a replaceable collection layer and a fan having a power supply such as a battery pack, all of which fits a small container, attachable to, e.g., the lapel of the user, means to rotate the fan and move the aerosol through the sampler, so as to draw airborne particles through the inlet and through one or more nozzles, to impact the particles on the layer for analysis of same.

4 Claims, 6 Drawing Sheets

COMPACT AEROSOL SAMPLER

STATEMENT OF GOVERNMENT INTEREST

The invention described herein may be manufactured and used by or for the Government for governmental purposes without the payment of any royalty thereon.

CROSS-REFERENCE TO RELATED PATENT APPLICATION

This Application is a substitute for application Ser. No. 11/223,316, now abandoned, which was filed on Sep. 12, 2005, of the same title and inventor.

FIELD OF THE INVENTION

This invention relates to an aerosol sampler, particularly a compact aerosol sampler that is readily portable.

BACKGROUND OF THE INVENTION

Typically, prior art aerosol collection instruments use filters in which air is drawn therethrough by means of a pump. A pump is used because the pressure drop across a filter rises sharply with particle loading. However, pumps are suitable for moving air across a large pressure drop, though in relatively small amounts.

Also pumps are relatively heavy and noisy and require a relatively large battery pack to power same if one is to have a portable unit.

Because of the weight of the above assembly, it is divided into two units to assist the wear-ability thereof. That is, the collection surface of the sampler is a filter inside a housing clipped, e.g., to the collar of the wearer, while the pump and battery pack are worn on the belt of the wearer and the two units are connected by, e.g., a plastic air hose, as illustrated in FIG. 6 hereof.

Typically the pump box and battery pack weigh a pound or more. Also the pump is relatively loud and rather noticeable if worn indoors, to the discomfort of the wearer.

That is, in prior art air samples, the inlet system is in the breathing zone of the wearer and the pumping system is worn at his waist, which can be for a period of several hours, to the further discomfort of the wearer. For related prior art samplers, see U.S. Pat. No. 5,693,895 to Baxter and U.S. Pat. No. 6,170,342 to Walter.

There has now been discovered a compact, light weight air sampler that is a one part rather than a two part unit, that is eminently wearable, less conspicuous and comfortable to wear for extended periods as further described below.

SUMMARY OF THE INVENTION

Broadly the present invention provides an aerosol sampler comprising, an aerosol inlet, an impactor at or below the inlet, the impactor having one or more nozzles therethrough, a collection layer below the impactor, a fan and means to rotate the fan and move aerosol through the sampler, so as to draw airborne particles through the inlet and through one or more nozzles, to impact the particles on the layer for analysis.

In a preferred embodiment, a pre-classifier 50 is mounted over the inlet 13 of the sampler 10, as shown in FIG. 3. The pre-classifier 50 screens out larger particles from entering such inlet, while the nozzles 20 of the impactor 18 below, control the lower limit of the size of particles impacting the collection layer 16 so as to collect particles on such layer in a desired size range as more fully described below.

In the prior art, pumps are used to compress and move relatively small amounts of fluid across a potentially large pressure drop. Also, pumps require considerably more power to operate than a fan and need a heavy battery assembly.

The present invention employs a fan which is used to move air across a relatively low-pressure drop.

By “fan” as used herein is meant bladed air movers such as fans and blowers, including a series of parallel blades arrayed in a drum or roller shape.

By “aerosol”, as used herein, is meant a suspension of fine, solid, liquid particles or pathogens and the like, in air, as smoke, fog or mist.

BRIEF DESCRIPTION OF THE DRAWINGS

The invention will become more apparent from the following detailed specification and drawings in which.

DESCRIPTION OF PREFERRED EMBODIMENTS

Figure 1:
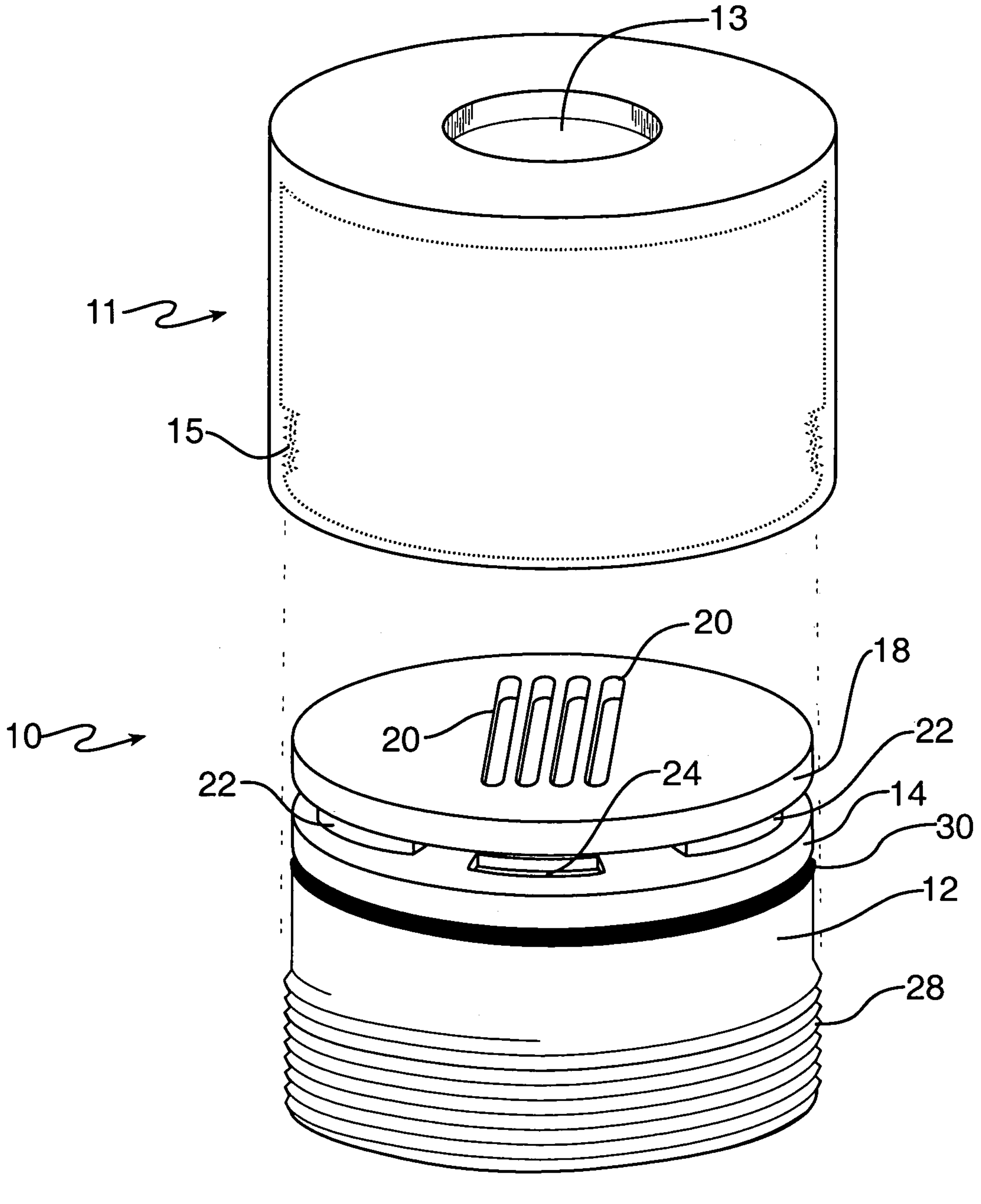
FIG. 1 is a perspective view of partly assembled components of the air sampler embodying the present invention.
Figure 2:
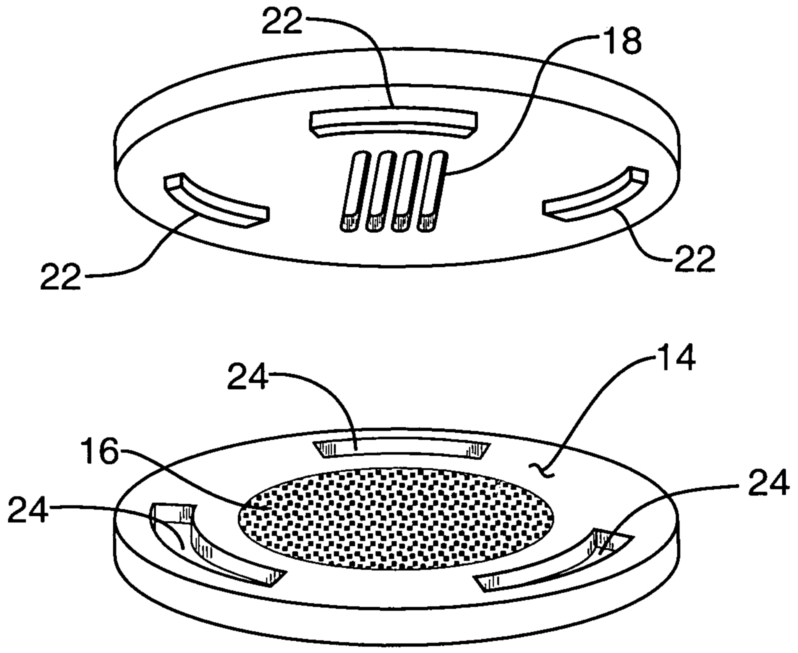
FIG. 2 is a partly exploded perspective view of some components of the air sampler embodying the present invention.
Figure 3:
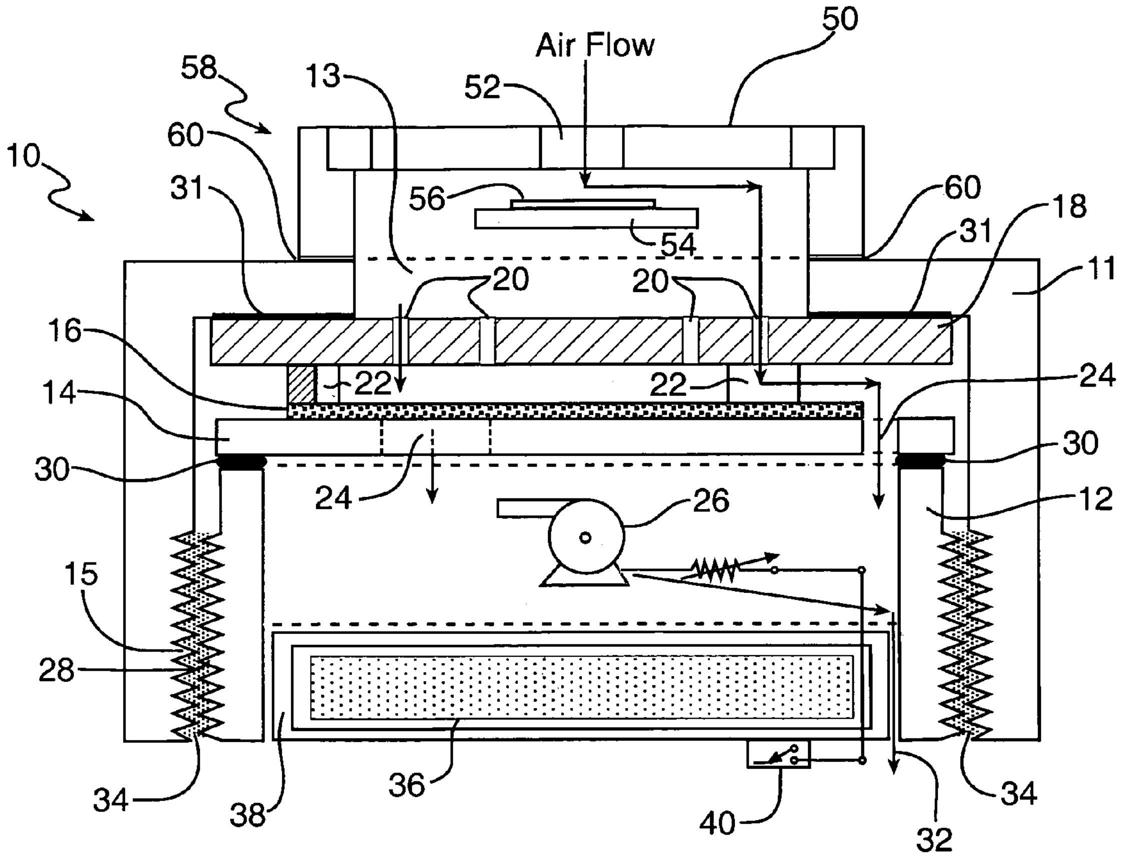
FIG. 3 is an elevation view, partly in section, of an air sampler assembly embodying the present invention.

Referring now to the present invention in detail, aerosol sampler 10 has fan housing 12, surmounted by impaction plate 14, collection layer 16, impactor 18 and cap 11, having inlet 13, as shown in FIGS. 1, 2 & 3.

The impactor 18 has one or more nozzles 20 therein, which can each be, e.g., slits 200 microns wide and six centimeters long, for airflow into the air sampler assembly, as indicated in FIGS. 1, 2 & 3.

The incoming air is impacted through the nozzles 20 onto the collection layer 16, as indicated in FIGS. 1,2 & 3.

The underside of the impacting disk 18 has several feet or stand-offs 22 to keep the nozzles 20 spaced at a distance from the collection layer 16 and its underlying support, impaction plate 14, as shown or indicated in FIGS. 2 & 3. The nozzles preferably have sufficient size, in cross-section, to permit aerosol flow therethrough at low pressure drop.

In between the standoffs 22 is sufficient space for air to flow, at low-pressure drop, through the passages 24 in the impaction plate 14, down to the next stage, as shown or indicated in FIGS. 2 & 3.

The collection layer 16 can be a thin flat material suitable for aerosol impaction and subsequent assay. Such layer 16 is sandwiched between the standoffs 22 of the impactor 18 and the impaction plate 14, as shown in FIG. 3.

As noted above, the impaction plate 14 has passages 24 to allow airflow, at low-pressure drop, to the fan housing 12 below, as shown in FIG. 3.

As to airflow rate, the width and length of the nozzles 20 are also sized to provide a suitable particle size impaction cut-off to limit the size or size range of the particles impacting on the collection layer 16, shown in FIGS. 2 & 3. This size or size range is set by the value of the Stokes no. for the impactor assembly. By Stokes No, as used herein, is meant the ratio of a particle's stopping distance at average nozzle exit velocity to the slit width.

In the fan housing 12 is the fan 26, which must support sufficient pressure drop (e.g., at less than 1" water column) to move air through the sampler assembly at the desired flow rate. By low pressure drop, through the inventive sampler assembly, as used herein, is meant 0.05 to 1 to 5" or more and preferably 0.1 to 2.0" water column, to move aerosol therethrough at the desired flow rate.

The impactor 18, collection layer 16 and impaction plate 14, are sandwiched between the cap 11 (having an air inlet 13) and, at the bottom thereof, interior threads 15, to mate with the exterior threads 28 of the fan housing 12, as shown or indicated in FIGS. 1 & 3. That is, the cap 11 and the fan housing 12 thread together, as shown in FIG. 3.

The air sampler assembly is sealed between the impaction plate 14 and the fan housing 12 by a grease coating or gasket 30 as sealant (which is also used as sealant 31 between cap 11 and impactor 18), while the space between housing threads 15 & 28 has a sealant, such as grease or plastic tape, e.g., of Teflon™, 34, as shown in FIG. 3.

Within the fan housing 12 and below the fan 26 is the battery 36, within the battery case 38, as is the flow control circuitry, for controlling the RPM of the fan and thus the flow rate of air through the aerosol mini-sampler of the Invention, which fan is activated by the on-off switch 40, shown in FIG. 3.

The battery is of sufficient capacity to power the fan 26 for, e.g., up to 8 hours, at an airflow rate of 10 or more liters per minute, although these parameters can also be reduced depending upon the sampling application.

Figure 4:
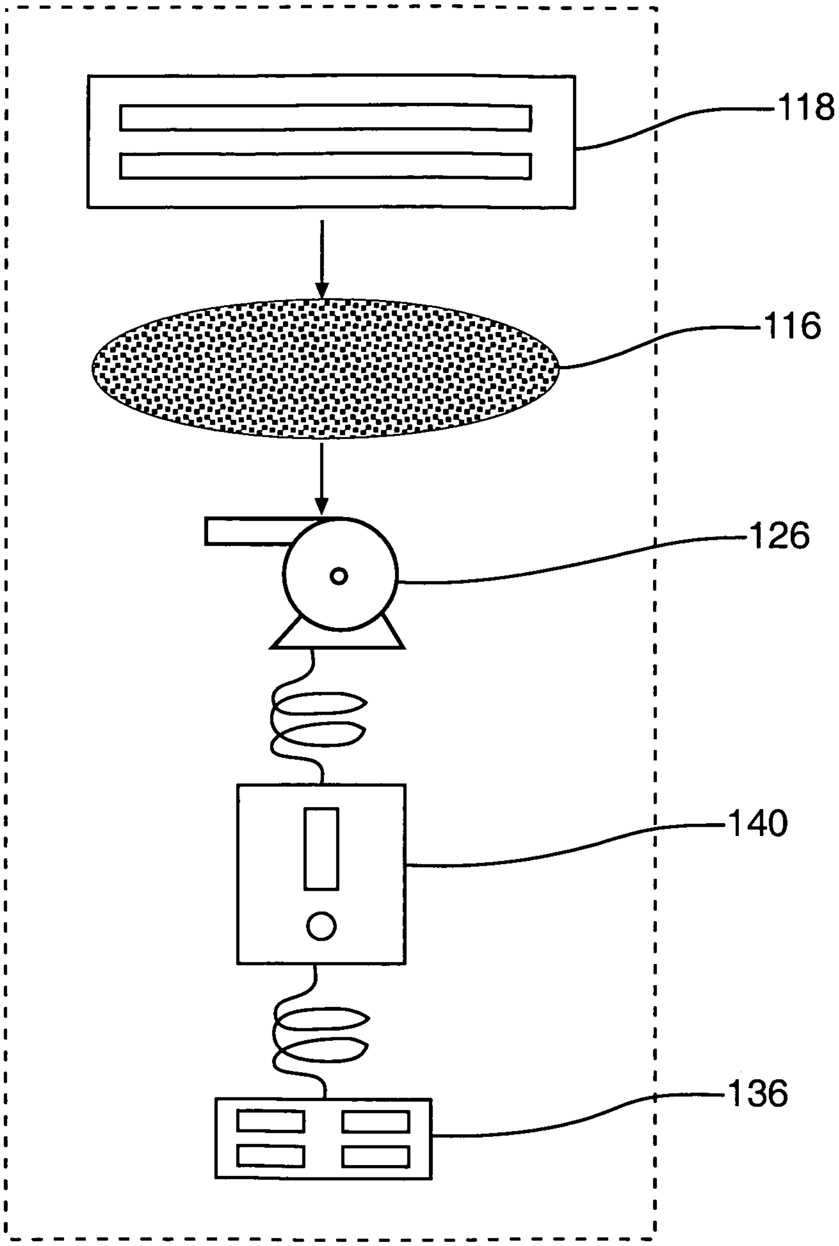
FIG. 4 is a schematic view of the air sampler embodiment, shown in FIG. 3.

A schematic of the aerosol mini sampler of the invention is shown in FIG. 4 hereof, in which important elements thereof are highlighted, such as the size classifying impactor nozzles 118 over the collection layer 116 and a fan 126, powered by battery 136, with airflow regulated by the electrical flow controller 140, as shown.

In a preferred embodiment, the sampler 10 has, mounted above the inlet 13, a pre-classifier 50, e.g., an impactor or a cyclone, to screen out relatively large particles, e.g., over 30 microns (μ) from entering the sampler. An impactor 18 having nozzles 20 is mounted at or below the inlet, per FIGS. 1 & 2, sized to impact particles, e.g., particles larger than 1μ onto the collection layer. Smaller particles do not so impact but go with the air flow to exhaust, e.g., at outlet 32 of FIG. 3. Therefore, the combined effect of the pre-classifier and the impactor is that particles in a defined size range, e.g., between 1 and 30μ, impact the collection layer. The nozzles 20 of the impactor can take various shapes such as round, angular, elongated, slits or a combination thereof.

Referring further to the pre-classifier 50, it has an inlet 52 with a plate 54 mounted below, within housing 58, per FIG. 3. The plate 54 has optionally, a sticky layer 56 thereon, to receive and adhere particles above a desired size, while smaller particles flow by. The housing 58 rests on seals 60 on cap 11 over the inlet 13 of the sampler 10, as shown in FIG. 3. Thus a desired particle size range can impact the collection layer in the inventive sampler, as described above.

Figure 5:
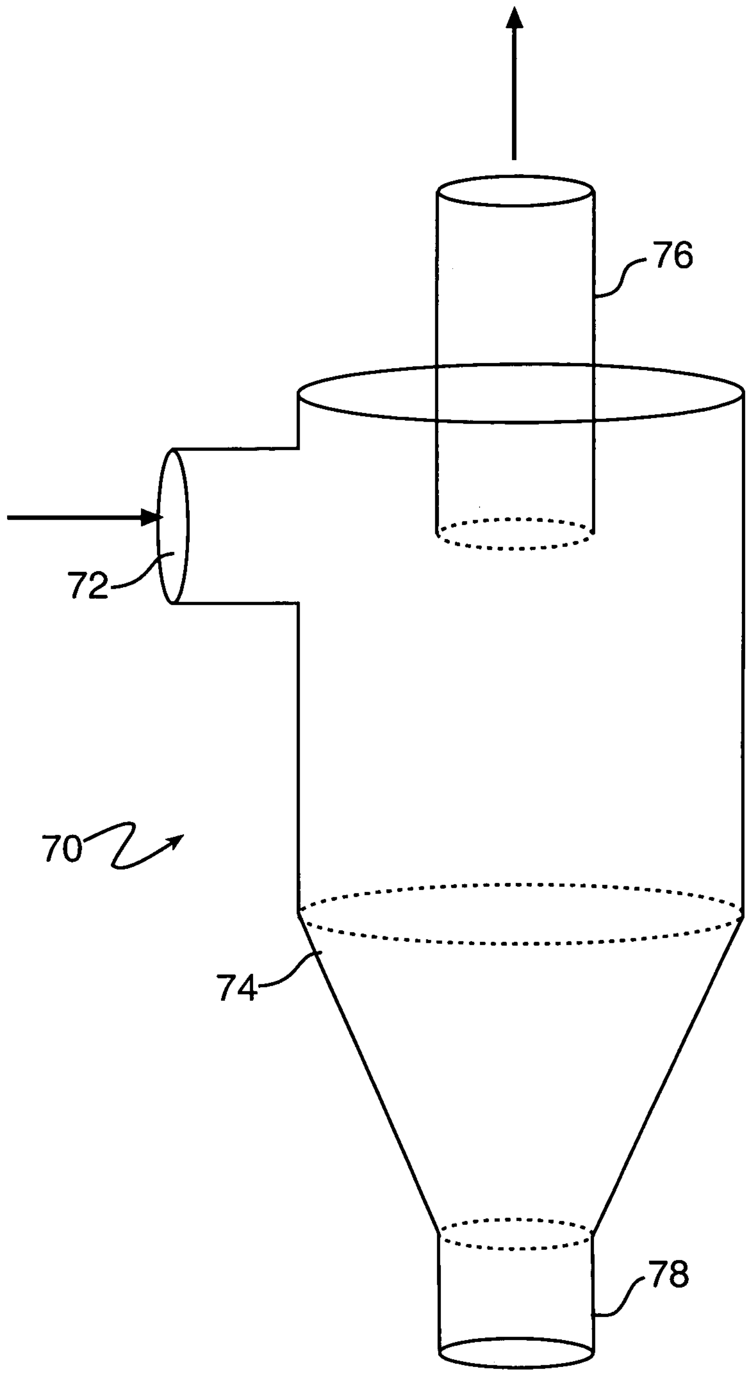
FIG. 5 is an elevation schematic view of a particle separator employed in the air sampler of the invention.

An alternate pre-classifier in the form of a cyclone can be employed, per the invention. As indicated in FIG. 5, a cyclone 70 is an apparatus in which particles are removed by centrifugal forces in a cyclonic path. Cyclone samplers use a vortical flow inside a cylindrical or conical chamber. Air is introduced tangentially near the top, at inlet 72, creating a double vortex flow within the cyclone body. The flow spirals down the outer portion of the chamber 74 and then reverses and spirals up the inner core to the exit tube 76 (which can feed such flow to the inlet 13 of the inventive sampler of FIG. 3.) Particles having excessive inertia are unable to follow the air streamlines, and they impact onto the cyclone walls or fall to the grit pot 78 at the bottom for discard.

Figure 6:
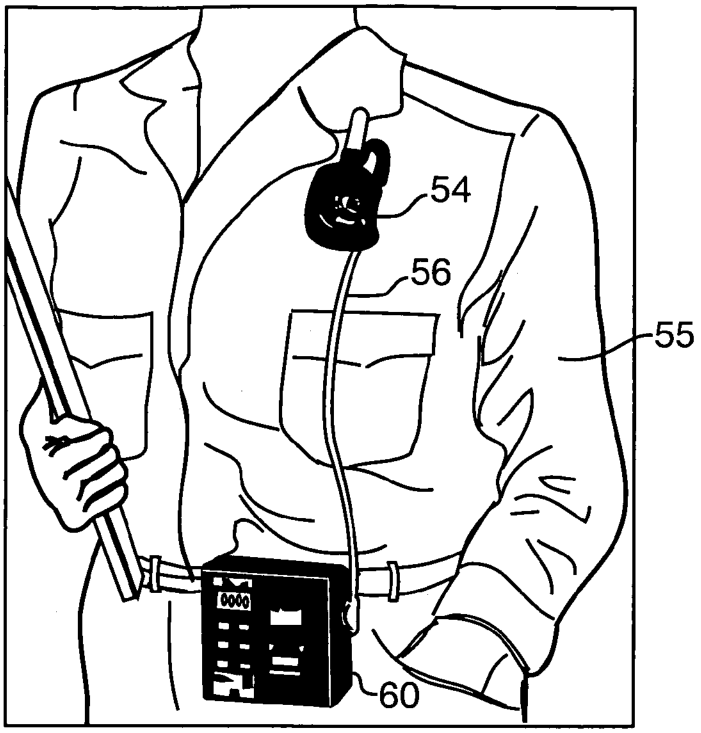
FIG. 6 is an air sampler of the prior art as worn by a tester.

A typical sampler of the prior art is shown, in operation, in FIG. 6 in which the air intake component 54, in the air breathing zone of wearer 55, is connected by tube 56, to a heavy package 60 containing flow pump & battery pack.

Figure 7:
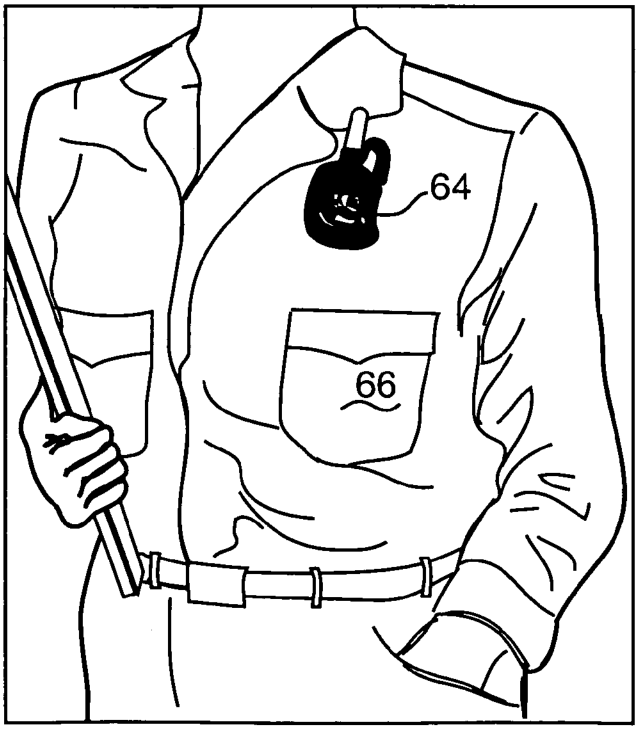
FIG. 7 is a fragmentary elevation view of the air sampler embodying the invention as worn by a tester.

In contrast, the aerosol mini sampler 64 of the present invention is shown in FIG. 7 as a self-contained compact unit without need of a tube connecting to a heavy battery pack per FIG. 6 hereof. Thus in the mini aerosol sampler of the present invention is found a unit that can be worn entirely in the breathing zone of the wearer 66, which sampler is capable of high airflow rates, e.g., over ten liters per minute, with relatively low power requirements since it is a fan and not a pump. That is, having both the inlet system and the airflow system combined in a single lightweight container is a major convenience. Convenience is important because such samplers are often worn by volunteers for an eight-hour shift, to obtain extensive air samples in the workplace or other environments, for which purpose a heavy and obtrusive pump system of the prior art is not conducive.

Novel features of the present invention include 1) the entire unit, with the, can be worn in the breathing zone of the user, 2) the combination of particle impaction with a fan, to produce a substantial air current in the inventive unit 3) that is a light weight, personal sampler with a flow rate of 10 or more liters per minute for several types of regulatory tests, which tests are presently done with bulky and stationery air samplers, for tests such as source apportionment, radioactive aerosol monitoring, testing for mold and the like and 4) also in the present unit, airflow particles accumulate on a collection layer, the layer is then removed from the inventive unit to be sent for laboratory analysis, while a new collection layer is installed in the inventive unit, for ready reuse.

The air inlet of the sampler the present invention can have an impactor with round, angular or slotted, including slit shaped, intake orifices or nozzles or a combination thereof. As noted previously, such nozzles are preferably of sufficient cross-sectional size for aerosol flow-through at low-pressure drop to permit relatively large flow rates therethrough, which, in turn, influences or limits the size of particles impacting the collection layer. In advance of such inlet there can be mounted, a particle pre-classifier, e.g., an impactor or cyclone system, as noted above, for removing unwanted large particles from the inflow.

With or without such pre-particle removal before the intake of the inventive aerosol sampler, a collection layer is positioned inside such inlet as described above and shown, e.g., as collection layer 16 in FIG. 3 hereof. As indicated in that figure, the inlet air flows by and around such collection layer or surface, while the airborne particles, of desired size or size range, impact on such layer for collection, removal and later analysis as noted above.

Typical impact or collection layers include fiber filters or membrane filters as well as thin pieces of metal foil or agar for collecting airborne biological samples.

The minimum size of particles that impact on the collection surface is determined largely by the width of the nozzles and the speed of the air flowing through them, such as through slits 20 in FIG. 3. That is, particles larger than the critical size are collected, the rest pass through the device with the airflow. The faster the air flowing through the slits, the smaller the critical size but the larger the pressure drop in the unit.

Preferred is an aerosol sampler that has a cap, impactor, impaction disk, collection layer, fan and battery and desirably, an attaching means, such as a clip, to provide a sampler that is lightweight. One that can be worn for an extended period of time, e.g., up to 8 hours or more. One that is capable of high flows, e.g., over ten liters per minute in which the particles can be collected onto a variety of collection layers for a variety of assays, including gravimetric management, chemical speciation and the like. As noted, the inventive sampler is preferably worn in the breathing zone of the wearer, i.e., in a sphere having a radius up to 3 ft. from the mouth and nose, with no wind and a radius of more than 3 ft. in a wind.

High flow rate aerosol samplers are needed for sensitive measurements. However the maximum flow rate for a prior art personal or wearable pump sampler, having two components connected by a hose, is about 4 liters per minute (Lpm). As noted above, the inventive fan mini sampler can deliver airflow of over ten liters per minute.

It appears that until now, no one has combined a slit impactor with a fan and a power supply into a self-contained, lightweight and compact unit. But this is what is accomplished by the mini aerosol sampler the present invention which can operate at airflow rates of 10-15 Lpm or more. Thus the inventive sampler can detect very low concentrations of aerosol with a unit that can be worn, e.g., on a lapel of the user, unobtrusively for extended periods.

In another embodiment, a plurality of impactors and collection layers can be arranged sequentially forming a cascade impactor. Such cascade impactors are used to determine the particle size distribution of aerosols. The particle size cut-off for each successive impactor is a smaller size than the preceding impactor and thus the preceding impactor acts as a pre-classifier to the succeeding impactor. A typical sequence of cut-offs in such a cascade impactor is 10μ, 2.5μ and 1μ.

Several commercial applications of the mini aerosol sampler of the invention are seen including:

Sensors for air pollution monitoring or monitoring of air quality, particularly for combustion and factory by-products.

Sensors for allergy confirmation for directly measuring the allergens the patient has been exposed to, instead of diagnoses by injecting patients with a matrix of allergens.

Sensors for personal sampling of respirable particulate matter as used in such fields as industrial hygiene, occupational health, and indoor air quality monitoring, including both residential and industrial monitoring.

Sensors for detecting chemical agents on particulates and bio-aerosol pathogens.

Sensors for detecting respirable radon decay products.

What is claimed is:

1. An aerosol sampler for impacting particles of a desired size range onto a single collection layer, comprising a self-contained sampler, including:

(a) a fan;

(b) a pre-classifier having an inlet sized to screen out particles larger than the desired size range;

(c) an impactor in a spaced relationship between the pre-classifier and the collection layer;

(d) passages through the impactor;

(e) single impaction plate for holding the single collection layer;

(f) wherein the single impaction plate allows a flow of air over the single collection layer and through openings in the impaction plate outside the collection layer;

(g) wherein the passages are sized and shaped, and the space between the impactor and the collection layer, are such that in an air flow caused by the fan, particles within the desired size range will preferentially strike the collection layer and particles smaller than the desired size range will preferentially flow past the collection layer; and, (h) a battery for powering the fan.

2. The aerosol sampler according to claim 1, further including a continuous sticky layer in a spaced relationship between the pre-classifier and impactor for further capturing particles larger than the desired size range.

3. An aerosol sampler for impacting particles of a desired size range onto a single collection layer, comprising a self-contained sampler, including:

(a) a fan;

(b) a pre-classifier comprising a cyclone sized and shaped such that, in an air flow caused by the fan, particles larger than the desired size range will preferentially exit away from toward the collection layer;

(c) a impactor in a spaced relationship between the pre-classifier and the collection layer;

(d) passages through the impactor;

(e) single impaction plate for holding the single collection layer;

(f) wherein the impaction plate allows a flow of air over the collection layer and through openings in the impaction plate outside the collection layer;

(g) wherein the passages are sized and shaped, and the space between the impactor and the collection layer, are such that in an air flow caused by the fan, particles within the desired size range will preferentially strike the collection layer and particles smaller than the desired size range will preferentially flow past the collection layer; and, (g) a battery for powering the fan.

4. The aerosol sampler according to claim 3, further including a continuous sticky layer in a spaced relationship between the pre-classifier and impactor for further capturing particles larger than the desired size range.

* * * * *